(12) United States Patent
Wilmink

(10) Patent No.: US 8,155,338 B2
(45) Date of Patent: Apr. 10, 2012

(54) EARPLUG FOR INSERTION INTO AN AUDITORY DUCT

(75) Inventor: Engbert Wilmink, Delft (NL)

(73) Assignee: Dynamic Ear Company B.V., Delft (NL)

( * ) Notice: Subject to any disclaimer, the term of this patent is extended or adjusted under 35 U.S.C. 154(b) by 734 days.

(21) Appl. No.: 12/280,416

(22) PCT Filed: Feb. 26, 2007

(86) PCT No.: PCT/NL2007/050078
§ 371 (c)(1),
(2), (4) Date: Nov. 7, 2008

(87) PCT Pub. No.: WO2007/097627
PCT Pub. Date: Aug. 30, 2007

(65) Prior Publication Data
US 2009/0220103 A1     Sep. 3, 2009

(30) Foreign Application Priority Data

Feb. 24, 2006  (NL) ...................................... 1031241

(51) Int. Cl.
*H04R 1/10*  (2006.01)
(52) U.S. Cl. .......................................... 381/74; 381/317
(58) Field of Classification Search .................... 381/74, 381/316, 317, 318
See application file for complete search history.

(56) References Cited

U.S. PATENT DOCUMENTS 5,832,094 A    11/1998  Le Her

| 2002/0080979 | A1 | 6/2002 | Brimhall et al. |
| 2003/0002688 | A1 | 1/2003 | Kanevsky et al. |
| 2003/0112987 | A1 | 6/2003 | Nordqvist et al. |

FOREIGN PATENT DOCUMENTS

| EP | 1 111 960 A2 | 6/2001 |
| GB | 2 074 817 A | 11/1981 |
| JP | 3-117995 U | 12/1991 |
| JP | 8-079897 A | 3/1996 |
| JP | 10-304485 A | 11/1998 |
| JP | 2000-298058 A | 10/2000 |
| JP | 2003-125481 A | 4/2003 |
| JP | 2003-198179 A | 7/2003 |
| JP | 2003-264885 A | 9/2003 |
| JP | 4-504795 B | 7/2005 |
| JP | 2005-244645 A | 9/2005 |
| WO | WO 2005/041831 A1 | 5/2005 |

OTHER PUBLICATIONS

International Search Report fro PCT/NL2007/050078 dated May 21, 2007.

*Primary Examiner* — Kevin M Picardat
(74) *Attorney, Agent, or Firm* — Leydig Voit & Mayer Ltd.

(57) ABSTRACT

An earplug is described for insertion in an auditory duct. The earplug includes a loudspeaker for connection to a playback device. When inserted in a user's ear, the loudspeaker is in acoustic communication with the ear's canal. A transmitter is provided that transmits ambient sound to the ear canal with an adjustable damping level. A regulating unit regulates a damping level depending on detection of control signals to the loudspeaker. When the user does not listen to, for instance, music of the playback device, the user can simply observe ambient sounds without removing the earplug from the ear.

14 Claims, 3 Drawing Sheets

EARPLUG FOR INSERTION INTO AN AUDITORY DUCT

FIELD OF THE INVENTION

The invention relates to an earplug for insertion into an auditory duct.

BACKGROUND

Such earplugs are known as so-called otoplasts which are adapted to an ear canal of a user or which have been formed according to certain predetermined standard shapes, all this in order to provide the sealing between the ear plug and the auditory duct to be as favourable as possible so that "leakage" of sound can be prevented. Hence, in closed form, such an earplug forms a virtually perfect sealing of the auditory duct, so that incoming sound is damped maximally.

The state of the art knows such earplugs, as described in, for instance, U.S. Pat. No. 5,832,094. In the known earplug, a loudspeaker installation is described for connection to a playback device, which loudspeaker is in acoustic communication with the ear canal (see, in particular, FIGS. 3 and 4 and corresponding description of said publication). Further, an acoustic canal is shown that can transmit an ambient sound in a damped manner.

By varying the length of the canal and/or the volume of an acoustic cavity, the damping properties can be determined. The damping shown is not adjustable. International patent publication WO2005041831 shows an acoustic canal with an adjustable acoustic valve. However, in this publication, no additional loudspeaker installation for coupling to a playback device is described.

SUMMARY OF THE INVENTION

The object of the invention is to provide an earplug with which a user can listen undisturbedly to music or information from the playback device, but with which at the same time, an easy and safe manner of hearing ambient sound is provided. This object is achieved through the features of claim 1. Through the provision of a device, with which a regulating device regulates the level of damping depending on detection of control signals to the loudspeaker, in particular, an earplug is provided with which, when he is not listening to music, the user can simply observe the ambient sounds without having to remove the earplug from his ear. Although various means are suitable for transmitting the ambient sound to the ear canal of the user, in particular through electronic transmission, this is preferably carried out by an adjustable acoustic valve as described in, for instance, the above-mentioned WO publication, for true-to-life representation of sound. Further, a user-operated unit for adjusting the damping level can be provided, for instance on the earplug, on the playback device or on a possible wire connection between playback device and earplug. This unit can comprise, for instance, an on/off button, the damping being adjusted independently of the control by the regulating unit. In particular, this on/off button can determine the active position of the adjustable damping, with which, in the on-position, the acoustic damping is cancelled and the valve in a position of rest. Conversely, in the off-position, the acoustic damping can be adjusted, with the valve also in a position of rest. Such adjustment can save electricity. The position of rest can also be adjusted gradually.

BRIEF DESCRIPTION OF THE DRAWINGS

Further features and advantages will be clarified on the basis of the drawings, which serve as illustration of the invention. In the drawings.

DETAILED DESCRIPTION OF THE DRAWINGS

Figure 1:
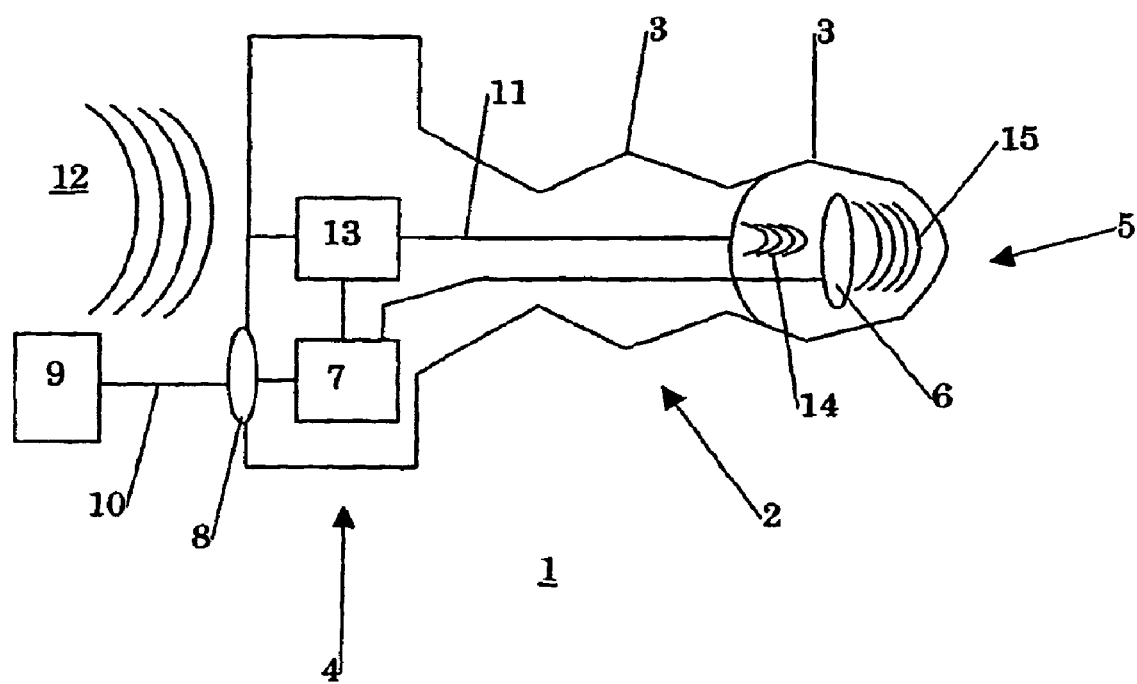
FIG. 1 shows a schematic representation of an exemplary embodiment according to the invention.

With reference to FIG. 1, an earplug 1 is shown for insertion in an auditory duct. To that end, the earplug comprises a tubular part 2 having a number of elastic thickenings 3 that serve for acoustically sealing the auditory duct. Alternatively, the earplug 1 can also be formed in a natural way, by a cast of the auditory duct, to be obtained in a known manner.

The earplug 1 comprises a rear part 4 in which receiving and regulating electronics 7 are accommodated which will be described in more detail in the following. Alternatively, the rear part 4 can be so narrow that this also fits within the auditory duct. At the front side 5, i.e. the side proximal to the middle ear, a loudspeaker device 6 is arranged. Alternatively, this may be provided further to the rear, towards the auditory duct, with an acoustic communication, for instance with a narrow tube. The loudspeaker device 6 is controlled by a receiving unit 7 which receives audio signals, via an input port 8, from an external source 9, for instance an MP3 player/radio/mobile phone or walkie-talkie. The reception can be wireless or via a wire 10.

Further, a transmitting means 11 is present for transmitting ambient sound 12. The transmitting means comprises a damping means 13 for regulating transmission in an adjustably damped manner. According to the invention, the damping means 13 is controlled depending on detection of control signals from receiving unit 7 to the loudspeaker 6. In an exemplary embodiment, the transmitting means can comprise a conventional microphone (not represented) and attenuation circuit, wherein an attenuated audio signal is transmitted to the loudspeaker in addition to, or as alternative to the audio signal provided by the receiving unit 7, all this depending on the control by receiving unit 7 of audio signals from the external source 9. In another exemplary embodiment, the ambient sound 12 is represented in attenuated form, as attenuated sound 14. This embodiment can utilize an acoustic valve as described in more detail in FIG. 2. This (attenuated) ambient sound can be represented as an alternative to or together with the loudspeaker sound 15 generated by the loudspeaker 6.

Figure 2:
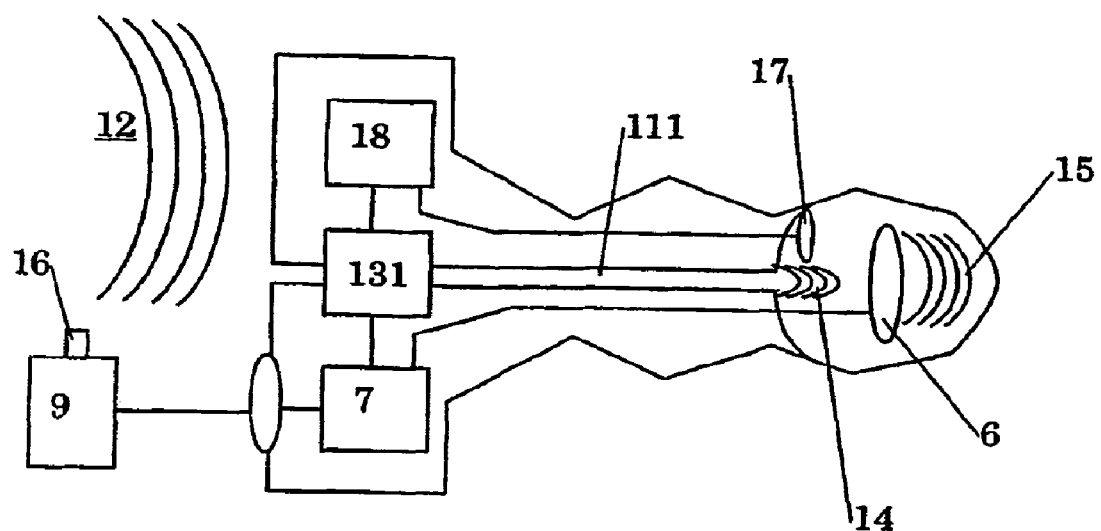
FIG. 2 shows a schematic representation of the example of FIG. 1 with an adjustable acoustic valve arranged therein.

FIG. 2 further shows an embodiment with an acoustic valve 131, all this as described in, for instance, WO2005041831. Such a valve is arranged in an open channel 111, forming an acoustic communication between the outside world and the ear canal. The channel 11 is adjustably pressed shut by the acoustic valve, resulting in damping of sound waves in the channel 111. In addition to the manner of control described with reference to FIG. 1, adjustment of the acoustic valve can be supplemented in various manners. Firstly, FIG. 2 shows that a user-operated unit 16 (for instance a button or rotating disc) is provided for adjusting the level of damping. Through adjustment thereof the user-operated unit 16 can set a position of rest of the damping, preferably, while the level of damping can be adjusted gradually. By setting the position of rest of the acoustic valve 131 for instance industrially, electricity can be saved. FIG. 2 further shows a microphone 17 which is connected to a regulating unit 18. Although the microphone can also be provided at the side remote from the middle ear (the rear side), the microphone is preferably disposed adjacent the side proximal to the middle ear because in this manner, a direct registration of the sound level near the middle ear can be obtained. Also, here, a level can be measured that is not to be exceeded when regulating the ambient sound 12. As a result, an accurate and optimal balance can be found with which the sound level can be controlled to a minimally understandable sound level, while simultaneously, a maximum noise volume is not exceeded. The regulating unit 18 adjusts the damping level of the acoustic valve 131 in response to ambient sound 12 registered by the microphone 17.

Figure 3:
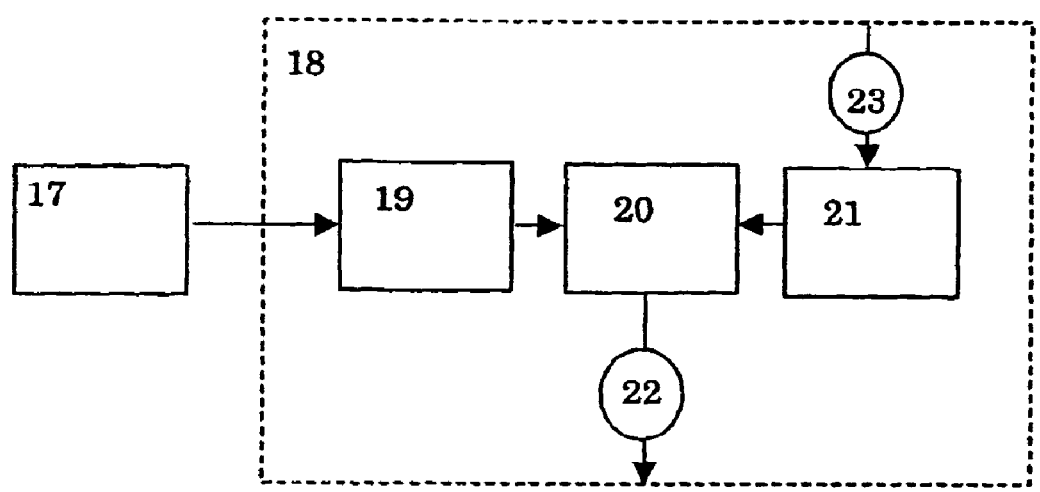
FIG. 3 shows an example of a schematic representation of steps of adjusting damping through sound profiles.

In the following, with reference to FIG. 3, the operation of the regulating unit 18 will be further elaborated, in particular the regulatory behaviour thereof in response to the received ambient sound 12. These aspects are of importance in connection with the adjustment of the acoustic valve in response to the reception of audio signals from the source 9, as described hereinabove, but can also, separately, be eligible for protection.

In particular, the regulating unit 18 comprises an analysing unit 19 for forming a sound profile of ambient sound registered by the microphone: the analysing unit having comparing means 20 for comparing the registered sound profile with stored sound profiles, for instance settings stored in a look up table 21; and giving a control instruction 22 to the damping means for adjusting the level of damping, depending on a setting instruction coupled to a stored sound profile that corresponds to the registered sound profile.

In yet a further embodiment, there is a provision in the regulating unit for configuration of the setting instructions 23 belonging to the stored sound profiles. To this end, for instance a communication port (not represented) can be present which communicates with a corresponding damping program that may run on a PC. In this manner, it is possible to define a sound profile on the basis of, for instance, the frequency and amplitude characteristics, and a corresponding, desired damping instruction. In one exemplary embodiment, such a profile can be created while, upon a sudden increase of the ambient sound level in, for instance, the acoustic domain of human speech, the level of damping is reduced. With such a use, monotonous sound can for instance be damped while at the moment a user is addressed, the damping is cancelled.

Although the invention is described with reference to the described embodiments, the invention is not limited thereto but can comprise various additions, in particular changes or modifications that are self-explanatory to the skilled person after reading this description. For instance, in the described embodiments, the starting point was damping through an acoustic valve. Other sound transmission systems are conceivable too, in particular electronic sound transmission. The earplug can further be of double design, and some functions can be distributed over two ears. Another variant can have functional parts such as microphone, loudspeaker and/or regulating unit accommodated in an external module which is communicatively coupled to the earplug according to the invention. Such additions are understood to be equivalent to and to lie within the framework of the following claims.

The invention claimed is:

1. An earplug for insertion into an auditory duct, comprising:
    a loudspeaker included in and/or outside the earplug for connection to a playback device, wherein the loudspeaker is in acoustic communication with the ear canal;
    a transmitter, comprising an acoustic channel with an adjustable acoustic valve arranged therein, for transmitting ambient sound to a user's ear canal at an adjustable damping level; and
    a regulating unit, included in and/or outside the earplug, for automatic regulation of the adjustable damping level of the transmitter depending on detection of control signals towards the loudspeaker.

2. An earplug according to claim 1, wherein the regulating unit is designed for regulating a sound level of the loudspeaker.

3. An earplug according to claim 1, wherein the regulating unit further comprises a user-operated unit for adjusting the adjustable damping level.

4. An earplug according to claim 3, wherein the user-operated unit sets a position of rest of the adjustable damping level.

5. An earplug according to claim 1, wherein the adjustable damping level provided by the regulating unit can be gradually adjusted.

6. An earplug according to claim 1, further comprising a microphone included in and/or outside the earplug; and wherein the regulating unit adjusts the adjustable damping level in response to ambient sound registered by the microphone.

7. An earplug according to claim 6, wherein the microphone is arranged adjacent a side of the earplug proximal to the user's middle ear.

8. An earplug according to claim 6, characterized in that the regulating unit for automatic regulation of the adjustable damping level, regulates a sound level of the loudspeaker and the adjustable damping level of the transmitter below a predetermined maximum sound level value.

9. An earplug according to claim 6, wherein the regulating unit includes an analyzing unit for forming a sound profile of ambient sound registered by the microphone; wherein the analyzing unit has comparing means for comparing the registered sound profile with stored sound profiles; and adjusts the adjustable damping level depending on a setting instruction which is coupled to a stored sound profile that corresponds to the sound profile of ambient sound registered by the microphone.

10. An earplug according to claim 9, wherein the analyzing unit executes an adjustable damping program defining setting instructions which are coupled to the stored sound profiles.

11. An earplug according to claim 9, wherein a sound profile corresponding to a sudden increase of the ambient sound level reduces the adjustable damping level.

12. An earplug according to claim 1, wherein a loudspeaker, microphone and/or regulating unit are included in an external module communicatively coupled to the earplug.

13. A method for damping ambient sound in an earplug to be inserted in an ear canal of a user, the earplug comprising an acoustic channel with an adjustable acoustic valve arranged therein, the method comprising:
    registering ambient sound;
    analyzing the registered ambient sound to determine a registered sound profile;
    comparing the registered sound profile with a predetermined set of stored sound profiles; and
    adjusting, via a regulating unit, included in and/or outside the earplug, for automatic regulation of the adjustable damping level of the acoustic channel, a damping of said acoustic channel which is coupled to a stored sound profile having the greatest similarity to the registered sound profile.

14. The method of claim 13 wherein the automatic regulation of the adjustable damping level depends on detection of control signals towards a loudspeaker included in and/or outside the earplug for connection to a playback device, wherein the loudspeaker is in acoustic communication with the ear canal.

* * * * *